US005965766A

United States Patent [19]

Chong et al.

[11] Patent Number: 5,965,766

[45] Date of Patent: Oct. 12, 1999

[54] PROCESS FOR SYNTHESIZING BENZOIC ACIDS

[75] Inventors: Joshua Anthony Chong, Lansdale; Fereydon Abdesaken, Dresher; Charles Chao Wu, North Wales, all of Pa.

[73] Assignee: Rohm and Haas Company, Philadelphia, Pa.

[21] Appl. No.: 09/017,176

[22] Filed: Feb. 2, 1998

Related U.S. Application Data

[63] Continuation-in-part of application No. 08/884,193, Jul. 1, 1997.

[60] Provisional application No. 60/026,642, Sep. 24, 1996.

[51] Int. Cl.[6] ...................... C07C 253/00; C07C 255/00; C07C 69/00; C07C 65/01

[52] U.S. Cl. .......................... 558/332; 558/343; 558/423; 560/130; 562/478

[58] Field of Search .................................... 558/343, 423, 558/332; 562/405; 560/130

[56] References Cited

U.S. PATENT DOCUMENTS 5,478,963 12/1995 Pfirmann et al. ........................ 558/343

*Primary Examiner*—Robert W. Ramsuer
*Assistant Examiner*—Joseph Murray
*Attorney, Agent, or Firm*—Clark R. Carpenter

[57] ABSTRACT

Nucleophilic substitution reactions on halobenzenes or triflyl substituted benzenes are carried out in the presence of catalysts. In particular the present invention provides a process leading to optionally substituted hydroxybenzoic, alkanoyloxybenzoic, formyloxybenzoic and alkoxybenzoic acids and optionally substituted hydroxybenzonitriles and alkoxybenzonitriles from substituted 2,6-dihalobenzenes, 2-halo-6-triflylbenzene and 2,6-ditriflylbenzenes.

59 Claims, No Drawings

PROCESS FOR SYNTHESIZING BENZOIC ACIDS

This application is a continuation-in-part of U.S. Ser. No. 08/884,193, filed on Jul. 1, 1997, which is a continuation-in-part of U.S. Ser. No. 60/026,642, filed on Sep. 24, 1996.

The present invention relates to a process for the manufacture of aromatic carboxylic acids and nitrites having an alkoxy, hydroxy, formyloxy or alkanoyloxy substituent on the aromatic ring.

In particular, benzoic acids or benzonitriles with an alkoxy, hydroxy, formyloxy or alkanoyloxy substituent on the aromatic ring are used for various commercial applications including the manufacture of agricultural and pharmaceutical chemicals. Although various routes are known, for example, conversion of an amino substituted benzoic acid or ester to an alkoxy or hydroxy substituted benzoic acid or ester using a diazotization reaction as described in U.S. Pat. No. 5,530,028, the conversion of 6-chloro-2-methoxytoluene to 3-methoxy-2-methylbenzoic acid using Grignard reaction conditions as described in AU-A-12496/83, or the hydrolysis of 3-methoxy-2-methylbenzonitrile to 3-methoxy-2-methylbenzoic acid as described by M. S. Carpenter et al. in *J. Org. Chem.* 20 (4), 401–411 (1955), there is a continuing need to provide these kinds of acids and nitrites at lower cost and higher purity. The present invention provides several advantageous routes to produce the desired benzoic acids and benzonitriles.

This invention provides a process for the preparation of a compound of formula (III) comprising the steps of (i) reacting a compound of formula (I) with an alkali or alkaline earth alkoxide, alkali or alkaline earth aroxide, alkali or alkaline earth arylalkoxide, or alkali or alkaline earth heteroarylalkoxide, optionally in the presence of a catalyst comprising copper, to provide a compound of formula (IIa)

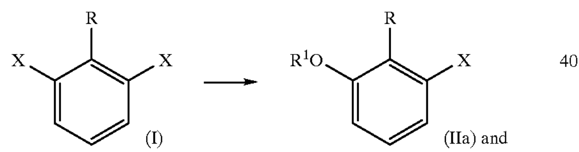

(ii) reacting a compound of formula (IIa) with an alkali or alkaline earth metal cyanide, an aldehyde or ketone cyanohydrin or hydrogen cyanide in the presence of a catalyst comprising nickel, cobalt, palladium or platinum, or reacting a compound of formula (IIa) with copper(I) cyanide in the optional presence of a catalyst comprising nickel, cobalt, palladium or platinum to form an aromatic cyano compound of formula (III)

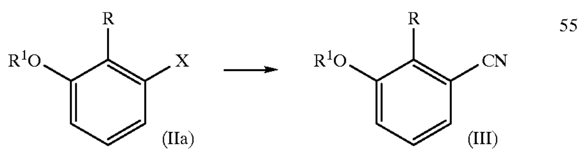

wherein each X is independently triflyl, chloro, bromo or iodo;

R is a hydrogen atom, $(C_1–C_6)$alkyl, aryl, aryl$(C_1–C_2)$alkyl, heteroaryl or heteroaryl$(C_1–C_2)$alkyl; or a $(C_1–C_6)$alkyl, aryl, aryl$(C_1–C_2)$alkyl, heteroaryl or heteroaryl$(C_1–C_2)$alkyl substituted with from one to three substituents independently selected from $(C_1–C_3)$alkyl and $(C_1–C_3)$alkoxy;

$R^1$ is $CHR^2R^3$, aryl, aryl$(C_1–C_2)$alkyl or heteroaryl $(C_1–C_2)$alkyl; or aryl, aryl$(C_1–C_2)$alkyl or heteroaryl $(C_1–C_2)$alkyl substituted with from one to three substituents independently selected from $(C_1–C_3)$ alkyl and $(C_1–C_3)$alkoxy; and $R^2$ and $R^3$ are each independently a hydrogen atom, $(C_1–C_5)$alkyl or $(C_1–C_3)$alkyl substituted with $(C_1–C_2)$alkoxy.

Alternatively, this invention provides a process for the preparation of a compound of formula (III) comprising the steps of (i) reacting a compound of formula (I) with an alkali or alkaline earth metal cyanide, an aldehyde or ketone cyanohydrin or hydrogen cyanide in the presence of a catalyst comprising nickel, cobalt, palladium or platinum, or reacting a compound of formula (I) with copper(I) cyanide in the optional presence of a catalyst comprising nickel, cobalt, palladium or platinum to form an aromatic cyano compound of formula (IIb)

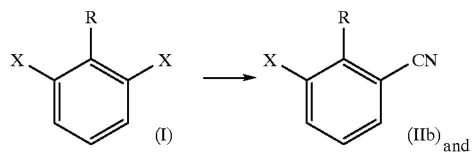

(ii) reacting a compound of formula (IIb) with an alkali or alkaline earth alkoxide, alkali or alkaline earth aroxide, alkali or alkaline earth arylalkoxide, or alkali or alkaline earth heteroarylalkoxide, optionally in the presence of a catalyst comprising copper, to provide a compound of formula (III)

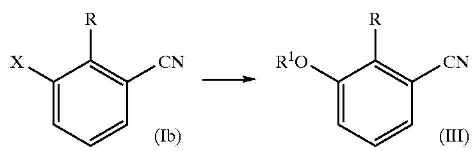

wherein each X is independently triflyl, chloro, bromo or iodo;

R is a hydrogen atom, $(C_1–C_6)$alkyl, aryl, aryl$(C_1–C_2)$ alkyl, heteroaryl or heteroaryl$(C_1–C_2)$alkyl; or a $(C_1–C_6)$alkyl, aryl, aryl$(C_1–C_2)$alkyl, heteroaryl or heteroaryl$(C_1–C_2)$alkyl substituted with from one to three substituents independently selected from $(C_1–C_3)$alkyl and $(C_1–C_3)$alkoxy;

$R^1$ is $CHR^2R^3$, aryl, aryl$(C_1–C_2)$alkyl or heteroaryl $(C_1–C_2)$alkyl; or aryl, aryl$(C_1–C_2)$alkyl or heteroaryl $(C_1–C_2)$alkyl substituted with from one to three substituents independently selected from $(C_1–C_3)$ alkyl and $(C_1–C_3)$alkoxy; and $R^2$ and $R^3$ are each independently a hydrogen atom, $(C_1–C_5)$alkyl or $(C_1–C_3)$alkyl substituted with $(C_1–C_2)$alkoxy.

This invention further comprises providing a process for the preparation of a compound of formula (IVa) by hydrolyzing a compound of formula (III) using a strong acid or base

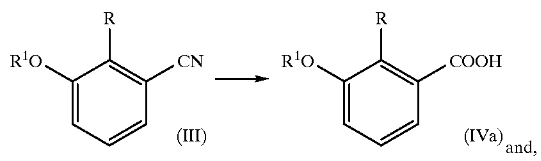

if desired, further converting a compound of formula (IVa) to a compound of formula (V) using an ether cleavage reagent

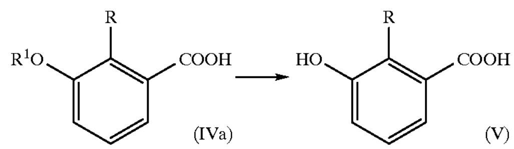

wherein

R is a hydrogen atom, $(C_1–C_6)$alkyl, aryl, aryl$(C_1–C_2)$alkyl, heteroaryl or heteroaryl$(C_1–C_2)$alkyl; or a $(C_1–C_6)$alkyl, aryl, aryl$(C_1–C_2)$alkyl, heteroaryl or heteroaryl$(C_1–C_2)$alkyl substituted with from one to three substituents independently selected from $(C_1–C_3)$alkyl and $(C_1–C_3)$alkoxy;

$R^1$ is $CHR^2R^3$, aryl, aryl$(C_1–C_2)$alkyl or heteroaryl$(C_1–C_2)$alkyl; or aryl, aryl$(C_1–C_2)$alkyl or heteroaryl$(C_1–C_2)$alkyl substituted with from one to three substituents independently selected from $(C_1–C_3)$alkyl and $(C_1–C_3)$alkoxy; and $R^2$ and $R^3$ are each independently a hydrogen atom, $(C_1–C_5)$alkyl or $(C_1–C_3)$alkyl substituted with $(C_1–C_2)$alkoxy.

Alternatively, this invention also further comprises providing a process for the preparation of a compound of formula (IVb) by reacting a compound of formula (III) with an ether cleavage reagent in a first step

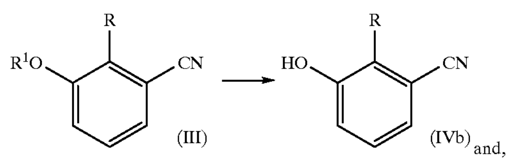

if desired, hydrolyzing a compound of formula (IVb) using a strong acid or base to a compound of formula (V) in a second step

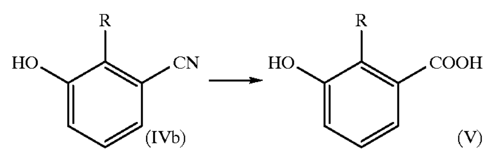

wherein

R is a hydrogen atom, $(C_1–C_6)$alkyl, aryl, aryl$(C_1–C_2)$alkyl, heteroaryl or heteroaryl$(C_1–C_2)$alkyl; or a $(C_1–C_6)$alkyl, aryl, aryl$(C_1–C_2)$alkyl, heteroaryl or heteroaryl$(C_1–C_2)$alkyl substituted with from one to three substituents independently selected from $(C_1–C_3)$alkyl and $(C_1–C_3)$alkoxy;

$R^1$ is $CHR^2R^3$, aryl, aryl$(C_1–C_2)$alkyl or heteroaryl$(C_1–C_2)$alkyl; or aryl, aryl$(C_1–C_2)$alkyl or heteroaryl$(C_1–C_2)$alkyl substituted with from one to three substituents independently selected from $(C_1–C_3)$alkyl and $(C_1–C_3)$alkoxy; and $R^2$ and $R^3$ are each independently a hydrogen atom, $(C_1–C_5)$alkyl or $(C_1–C_3)$alkyl substituted with $(C_1–C_2)$alkoxy.

This invention further contemplates providing a process for the preparation of a compound of formula (V) by reacting a compound of formula (III) in a single step with a strong acid which acts both as an ether cleavage reagent and as a nitrile hydrolysis reagent

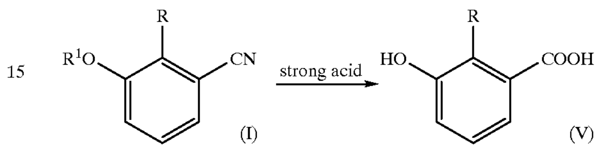

wherein

R is a hydrogen atom, $(C_1–C_6)$alkyl, aryl, aryl$(C_1–C_2)$alkyl, heteroaryl or heteroaryl$(C_1–C_2)$alkyl; or a $(C_1–C_6)$alkyl, aryl, aryl$(C_1–C_2)$alkyl, heteroaryl or heteroaryl$(C_1–C_2)$alkyl substituted with from one to three substituents independently selected from $(C_1–C_3)$alkyl and $(C_1–C_3)$alkoxy;

$R^1$ is $CHR^2R^3$, aryl, aryl$(C_1–C_2)$alkyl or heteroaryl$(C_1–C_2)$alkyl; or aryl, aryl$(C_1–C_2)$alkyl or heteroaryl$(C_1–C_2)$alkyl substituted with from one to three substituents independently selected from $(C_1–C_3)$alkyl and $(C_1–C_3)$alkoxy;

$R^2$ and $R^3$ are each independently a hydrogen atom, $(C_1–C_5)$atkyl or $(C_1–C_3)$alkyl substituted with $(C_1–C_2)$alkoxy, and the strong acid is an aqueous solution of hydrobromic acid or hydroiodic acid.

This invention also further contemplates providing a process for the preparation of a compound of formula (VI) by reacting a compound of formula (V), as prepared in any of the processes described hereinabove, with an organic acid anhydride

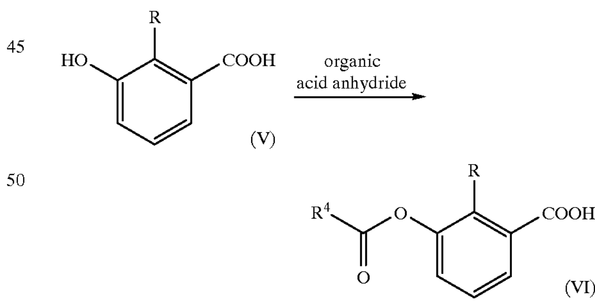

wherein

R is a hydrogen atom, $(C_1–C_6)$alkyl, aryl, aryl$(C_1–C_2)$alkyl, heteroaryl or heteroaryl$(C_1–C_2)$alkyl; or a $(C_1–C_6)$alkyl, aryl, aryl$(C_1–C_2)$alkyl, heteroaryl or heteroaryl$(C_1–C_2)$alkyl substituted with from one to three substituents independently selected from $(C_1–C_3)$alkyl and $(C_1–C_3)$alkoxy;

$R^4$ is a hydrogen atom or $(C_1–C_3)$alkyl; and the organic acid anhydride is formic anhydride, acetic anhydride, a propionic anhydride or a butyric anhydride.

This invention further embraces all the previously described process embodiments leading to compounds of formula (III), (IVa), (IVb), (V) and (VI) wherein the starting materials are compounds of formula (IIa) or (IIb) rather than a compound of formula (I).

The present invention is summarized conveniently by Diagram 1:

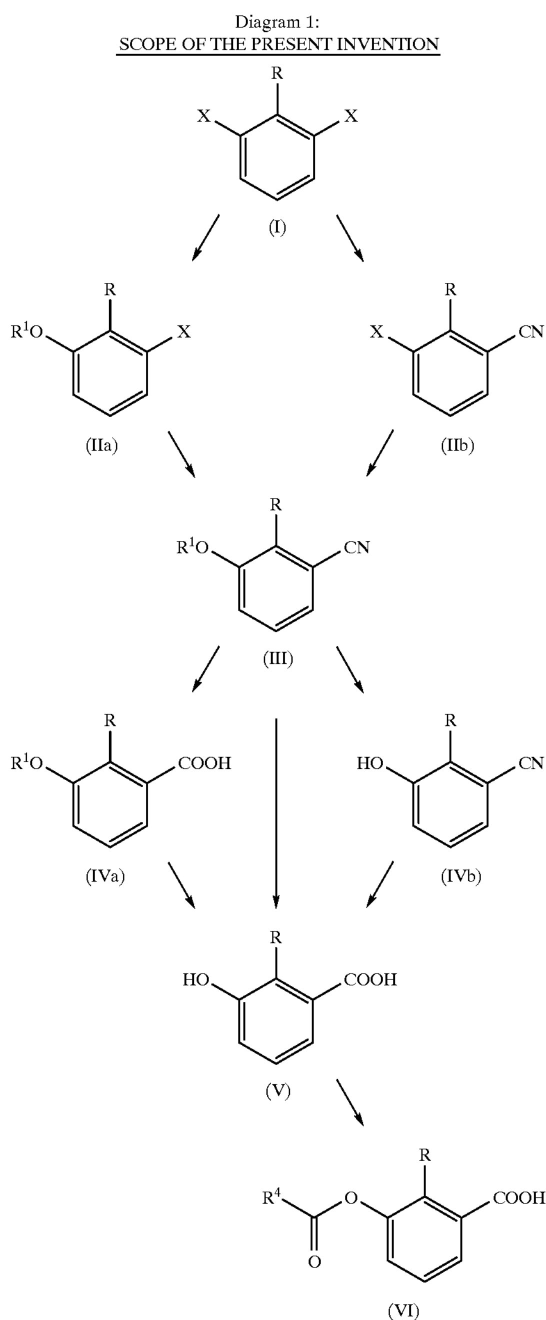

In all the alternative embodiments of this invention described previously, preferred processes are those wherein each X is independently chloro or bromo;

R is a hydrogen atom or $(C_1-C_6)$alkyl;

$R^1$ is $CHR^2R^3$, aryl or aryl$(C_1-C_2)$alkyl;

$R^2$ and $R^3$ are each independently a hydrogen atom or $(C_1-C_2)$alkyl, or $(C_1-C_2)$alkyl substituted with methoxy; and $R^4$ is $(C_1-C_3)$alkyl.

More preferred processes are those wherein each X is chloro, R is a hydrogen atom or $(C_1-C_3)$alkyl, $R^1$ is $CHR^2R^3$, $R^2$ and $R^3$ are each independently a hydrogen atom or $(C_1-C_2)$alkyl, and $R^4$ is $(C_1-C_2)$alkyl.

Even more preferred processes are those wherein R is methyl or ethyl, $R^2$ is a hydrogen atom, $R^3$ is a hydrogen atom or methyl, and $R^4$ is methyl.

As used herein, the term "alkyl" refers to straight and branched aliphatic hydrocarbon chains, for example, methyl, ethyl, n-propyl, isopropyl, n-butyl, sec-butyl, tert-butyl, isoamyl and n-hexyl.

The term "alkoxy" refers to straight and branched aliphatic hydrocarbon chains attached to an oxygen atom, for example, methoxy, ethoxy, n-propoxy, isopropoxy and the like.

The term "aryl" refers to an aromatic ring system, for example, phenyl, 1-naphthyl, 2-naphthyl and the like.

The term "arylalkyl" refers to an aryl group which is attached to an alkylene group, for example, benzyl, phenethyl and the like.

The term "heteroaryl" refers to aromatic heterocyclic groups. Heteroaryl rings and the heteroaryl moieties of other groups, such as heteroarylalkyl, are typically 5 or 6 membered aromatic rings containing one or more O, N, or S atoms which may be fused to one or more other aromatic, heteroaromatic or heterocyclic rings such as a benzene ring. Examples of heteroaryl groups include, but are not limited to, thienyl, furyl, pyrrolyl, triazolyl, thiazolyl, oxazolyl, isoxazolyl, thiazolyl, isothiazolyl, pyridyl, pyrimidinyl, pyrazinyl, pyridazinyl, triazinyl, benzofuranyl, benzothienyl, indolyl, quinazolinyl, acridinyl, purinyl and quinoxalinyl.

The term "heteroarylalkyl" refers to a heteroaryl group which is attached to an alkylene group, for example, furfuryl, thenyl, nicotinyl and the like.

The term "triflyl" refers to the trifluoromethanesulfonyl group $(CF_3SO_2)$.

The term "alkali" refers to a lithium, potassium or sodium atom.

The term "alkaline earth" refers to a magnesium, calcium, barium or strontium atom.

The monoalkoxylation or monoaroxylation reaction, which is used either to convert a compound of formula (I) to a compound of formula (IIa) or to convert a compound of formula (IIb) to a compound of formula (III), can be performed with or without a catalyst being present. When a catalyst is employed, suitable ones comprise copper and include copper(I) chloride, copper(I) bromide, copper(I) iodide, copper(I) cyanide, copper(II) chloride, copper(II) oxide, copper(II) sulfate and elemental copper. Copper(I) cyanide is a preferred catalyst. The catalyst comprising copper can be in many forms such as powders or copper deposited on carriers of which powders are especially preferred. When the catalyst is utilized, the usage rate is from 0.1 to 100 mole percent, based on the compound of formula (I) or of formula (IIb). The preferred usage rate is from 0.5 to 25 mole percent. A more preferred usage rate is from 1 to 10 mole percent.

There are many suitable carriers which can be used to support the copper catalyst including, but not limited to, silica, carbon, alumina, calcium carbonate and the like.

Suitable alkali and alkaline earth alkoxide reagents, used either to convert a compound of formula (I) to a compound of formula (IIa) or to convert a compound of formula (IIb) to a compound of formula (III), include, but are not limited to sodium methoxide, potassium methoxide, sodium ethoxide, magnesium methoxide, barium methoxide, calcium ethoxide, strontium ethoxide and the like. Similarly, suitable alkali and alkaline earth aroxides include sodium phenoxide, potasium phenoxide, lithium phenoxide, calcium phenoxide, magnesium phenoxide and the like. Suitable alkali and alkaline earth arylalkoxides include sodium benzoxide, calcium benzoxide and the like. Suitable alkali and alkaline earth heteroarylalkoxides include potassium thenoxide and the like. The alkali and alkaline earth alkoxides, aroxides, arylalkoxides and heteroarylalkoxides are usually used in the amount of from 100 to 200 mole percent based upon the aromatic compound substituted with halo or triflyl.

The process of this invention permits the selective replacement of a single halo or triflyl group on the aromatic ring of a compound of formula (I) with an alkoxy, aroxy, arylalkoxy or heteroarylalkoxy group. As an example, the present invention is able to monoalkoxylate, monoaroxylate, monoarylalkoxylate or monoheteroarylalkoxylate a 1-alkyl-2,6-dihalobenzene to a 1-alkyl-6-(alkoxy or aroxy or arylalkoxy or heteroarylalkoxy)-2-halobenzene with greater than 80% selectivity. Using preferred conditions, the selectivity is greater than 85%. Under more preferred conditions, the selectivity is greater than 90%. As is known to those of ordinary skill in the art, higher selectivities are commonly achieved at lower conversions. For example, when 2,6-dichlorotoluene is reacted with a methoxide, the selectivity to 6-chloro-2-methoxytoluene is greater than 99% at 70% conversion. When the conversion increases to 93%, the selectivity decreases to about 95%.

The reaction rate for the displacement of a single halo or triflyl group is enhanced if a suitable solvent or mixture of solvents is employed. Dimethyl sulfoxide (DMSO), dimethylformamide (DMF), 1-methyl-2-pyrrolidinone (NMP), dimethyl sulfate, ethyl acetate and suitable alcohols, such as methanol and ethanol, are preferred solvents, with DMSO and NMP being more preferred. The reaction is usually conducted at a temperature from 65 to 160° C., preferably higher than 90° C.

The cyanation reaction, which is used either to convert a compound of formula (I) to a compound of formula (IIb) or to convert a compound of formula (IIa) to a compound of formula (III), is typically performed in the presence of a catalyst comprising nickel, cobalt, palladium or platinum unless a large excess of copper(I) cyanide is utilized in which case the use of additional catalyst is optional. Such catalysts include, but are not limited to, a mixture of nickel(II) bromide, zinc and triphenylphosphine, a mixture of dibromobis(triphenylphosphine)nickel, zinc and triphenylphosphine, a mixture of dichlorobis (triphenylphosphine)nickel, zinc and triphenylphosphine and tris(triphenylphosphine)nickel. Combinations of these commercially available catalysts may also be used. The catalysts normally are employed in the amount of from 1 to 10 mole percent based upon the amount of the aromatic compound substituted with halo or triflyl.

Suitable cyanating reagents include, but are not limited to, sodium cyanide, potassium cyanide, lithium cyanide, calcium cyanide, cyanohydrins such as acetone cyanohydrin and acetaldehyde cyanohydrin, hydrogen cyanide, copper(I) cyanide and the like. Typically the cyanating reagent is employed in the amount of from 100 to 200 percent molar equivalents based upon the aromatic compound substituted with halo or triflyl.

A suitable solvent is often employed for the cyanation reaction. Alcohols, such as methanol and ethanol, tetrahydrofuran (THF), hexamethylphosphoramide (HMPA), acetonitrile (ACN), 1-methyl-2-pyrrolidinone (NMP), toluene and other aromatic solvents can be used. Mixtures of the appropriate solvents may also be employed. The preferred solvents are THF, NMP and ACN. The cyanation reaction is performed at temperatures from 20 to 220° C., preferably from 30 to 180° C. and more preferably from 40 to 140° C. The cyanation reaction generally results in yields of greater than 50%. Using preferred conditions, yields of greater than 75% are obtained. Using more preferred conditions, yields of greater than 90% by weight based upon the starting material are realized.

The hydrolysis of an aromatic cyano compound of formula (III) to an acid of formula (IVa) or the hydrolysis of an aromatic cyano compound of formula (IVb) to an acid of formula (V) can be conducted using conditions known to those with ordinary skill in the art. The reaction normally is performed in the presence of either a strong acid or a strong base. Suitable acids include strong mineral acids, such as hydrochloric acid, sulfuric acid, and phosphoric acid, of which sulfuric acid is preferred. Suitable bases include sodium hydroxide and potassium hydroxide. The hydrolysis reactions can be performed at temperatures from ambient to 180° C.

The ether cleavage reaction can be conducted using reactions known to those with ordinary skill in the art. For example, this reaction is performed by heating a compound of formula (III) with a Brønsted acid such as hydrochloric acid, hydrobromic acid or hydroiodic acid, with a Lewis acid such as boron trifluoride etherate, with a base such as sodium methoxide, pyridine or methylamine, or with a strong acid-weak base salt such as pyridine hydrochloride to form a hydroxy substituted compound of formula (IVb). Appropriate reaction temperatures can be from ambient to over 200° C. In a similar manner, a compound of formula (IVa) can be converted to a compound of formula (V).

The one step ether cleavage/nitrile hydrolysis for converting a compound of formula (III) to a compound of formula (V) is performed by heating a compound of formula (III) with an aqueous Brønsted acid such as hydrobromic acid or hydroiodic acid. A reaction temperature of from about 75° C. to about 275° C. is generally employed, with from about 125° C. to about 225° C. being a preferred range. Super atmospheric pressure is generally utilized to achieve such preferred temperatures and consequently minimize the reaction time.

The reaction of a compound of formula (V) with an organic acid anhydride to form a compound of formula (VI) is generally performed at a reaction temperature of from about 0° C. to about 150° C., preferably from about 10° C. to about 100° C. and more preferably from about 15° C. to about 75° C. Any solvent which does not participate in the desired esterification reaction is acceptable. The esterification can be run with or without a catalyst being present. When a catalyst is employed, it is most usually selected from a tertiary amine, for example pyridine, quinoline, a picoline, N-methylpyrrole, N-methylpyirrolidine or a trialkylamine such as triethylamine. Preferred catalysts are pyricline and triethylamine.

The following examples and experimental procedures are provided for guidance to the practitioner and are not meant to limit the scope of the invention which is defined by the claims.

EXAMPLE 1

Methoxylation of 2,6-Dichlorotoluene (DCT) to 6-Chloro-2-methoxytoluene (MCT)

To a 500 milliliter (mL) flask, equipped with a temperature controller, a condenser, and a magnetic stirrer, were charged 50 grams (g) of DCT (0.31 mol), 30 g of 95% potassium methoxide (0.41 mol), and 25 g of 1-methyl-2-pyrrolidinone (NMP). The mixture was stirred at 100° C. for 2 hours, and then at 120° C. for 18 hours. Dimethyl sulfate (10 g, 0.08 mol) was then added, and the resulting mixture was further stirred at 120° C. for 5 hours. After this period, the mixture was cooled to ambient temperatures and filtered. The filter cake was washed with isopropanol (3×65 mL). Analysis of the combined filtrate and washes showed that 40 g of MCT was generated. Yield: 82%.

EXAMPLE 2

Methoxylation of DCT Using CuCN in DMF

To a 25 mL flask, equipped with a temperature controller, a condenser, and a magnetic stirrer, were charged 2.00 g of DCT (12.4 mmol), 1.30 g of $NaOCH_3$ (24.1 mmol), 0.10 g of CuCN (1.2 mmol), and 10.0 g of DMF. The mixture was heated to 120° C. and stirred under nitrogen. Gas chromatography (GC) analysis showed that after 17 hours, the yield of MCT was 88.6%, with 10.0% of DCT left. The yield of MCT increased to 92.8% after 19 hours, with 1.4% of DCT still unreacted.

EXAMPLE 3

Methoxylation of DCT Using CuCN in DMF

To a 25 mL flask, equipped with a temperature controller, a condenser, and a magnetic stirrer, were charged 5.00 g of DCT (31.0 mmol), 2.00 g of $NaOCH_3$ (37.0 mmol), 0.15 g of CuCN (1.7 mmol), and 5.00 g of DMF. The mixture was heated to 150° C. and stirred under nitrogen. GC analysis showed that after 17 hours, the yield of MCT was 64.8%, with 28.1% of DCT left. The yield of MCT increased to 76.0% after 26 hours, when 16.3% of DCT was still unreacted.

EXAMPLE 4

Methoxylation of DCT Using CUCN in DMSO

To a 25 mL flask, equipped with a temperature controller, a condenser, and a magnetic stirrer, were charged 5.00 g of DCT (31.0 mmol), 2.00 g of $NaOCH_3$ (37.0 mmol), 0.15 g of CuCN (1.7 mmol), and 5.0 g of DMSO. The mixture was heated to 140° C. and stirred under nitrogen. GC analysis showed that after 6 hours, the yield of MCT was 82.8%, with 12.4% of DCT left. The yield of MCT increased to 86.1% after 12 hours, when 7.2% of DCT was still unreacted.

EXAMPLE 5

Methoxylation of DCT Using CuBr in methanol

To a 25 mL flask, equipped with a thermometer, a condenser, and a magnetic stirrer, were charged 2.00 g of DCT (12.4 mmol), 5.00 g of 25% $NaOCH_3$ solution (in methanol, 23.1 mmol), 0.25 g of CuBr (1.7 mmol), and 0.44 g of ethyl acetate. The mixture was heated to reflux and stirred under nitrogen. GC analysis showed that after 5 hours, the yield of MCT was 7.3%, with 92.1% of DCT left. The yield of MCT increased to 25.2% after 24 hours, when 65.2% of DCT was still unreacted.

EXAMPLE 6

Cyanation Reaction to Convert MCT to 2-Cyano-6-methoxytoluene

To a 50 mL, 3-necked flask, equipped with a reflux condenser, a magnetic stirrer, and a temperature controller, were added nickel(II) bromide (0.22 g, 1.0 mmol), zinc powder (0.20 g, 3.0 mmol), triphenylphosphine (1.31 g, 5.0 mmol), and 15 mL of tetrahydrofuran. The mixture was heated to 50° C. and stirred under nitrogen for 30 minutes. After this period, 6-chloro-2-methoxytoluene (4.70 g, 30.0 mmol) was added, and the temperature was raised to 60° C. The mixture was then stirred for another 30 minutes. Then, potassium cyanide (2.65 g, 40.7 mmol) was added gradually in 10 equal portions over a period of 5 hours. Upon the completion of the addition, the mixture was stirred at 60° C. for 18 hours. GC analysis showed that at the end of this period the composition of the reaction mixture was 71.5% of 2-cyano-6-methoxytoluene, 22.8% of 6-chloro-2-methoxytoluene, 4.1% of 2-methoxytoluene, and 0.5% of 2,2'-dimethyl-3,3'-dimethoxybiphenyl. The cyanation yield based on the consumed starting material was 92.6%.

EXAMPLE 7

Cyanation of 6-Chloro-2-methoxytoluene (MCT) to 2-Cyano-6-methoxytoluene (CMT)

Procedure 1 (CCW09-18):

To a 50 mL, 3-necked flask, equipped with a reflux condenser, a magnetic stirrer and a temperature controller were added dibromobis(triphenylphosphine)nickel (1.00 g, 1.34 mmol), zinc powder (0.25 g, 3.82 mmol), triphenylphosphine (1.50 g, 5.72 mmol), 6-chloro-2-methoxytoluene (MCT, 10.0 g, 63.8 g), 15.0 g of 1-methyl-2-pyrrolidinone (NMP) and 7.5 g of acetonitrile. The flask was purged with nitrogen for 5 minutes. The mixture was then heated to 60° C. and stirred under nitrogen for 30 minutes. After this period, the temperature was raised to 70° C., and potassium cyanide (8.5 g, 130 mmol, ground) was added in small portions over a period of 4 hours. Upon the completion of the addition, the resulting mixture was stirred at 70° C. for 18 hours. GC analysis showed that at the end of this period the composition of the mixture was (area % by FID): 2-cyanotoluene (CT) 3.45%, MCT 5.91%, 2-cyano-6-methoxytoluene (CMT) 90.30%.

Procedure 2 (CCW09-50):

To a 50 mL, 3-necked flask, equipped with a reflux condenser, a magnetic stirrer and a temperature controller were added dibromobis(triphenylphosphine)nickel (1.00 g, 1.34 mmol), zinc powder (0.30 g, 4.59 mmol), triphenylphosphine (1.50 g, 5.72 mmol), and 7.5 g of acetonitrile. The flask was purged with nitrogen for 5 minutes. The mixture was then heated to 60° C. and stirred under nitrogen for 30 minutes. After this period, a MCT-NMP mixture, containing 10 g of MCT (63.8 mmol) and 6.3 g of NMP (63.5 mmol), was added and the mixture was stirred for an additional 15 minutes. Then potassium cyanide (8.5 g, 130 mmol, ground) was added in small portions over a period of 4 hours. Upon the completion of the addition, the temperature was raised to 70° C., and the resulting mixture was stirred for an additional 16 hours. GC analysis (HP-35, 15 m column) showed that at the end of this period the composition of the mixture was (area % by FID): CT 1.28%, MCT 3.37%, CMT 92.60%, 2,6-dimethoxytoluene (DMT) 2.13%.

Procedure 3 (CCW09-52):

To a 50 mL, 3-necked flask, equipped with a reflux condenser, a magnetic stirrer and a temperature controller were added dibromobis(triphenylphosphine)nickel (1.00 g, 1.34 mmol), zinc powder (0.30 g, 4.59 mmol), triphenylphosphine (1.50 g, 5.72 mmol), and 7.5 g of acetonitrile. The flask was purged with nitrogen for 5 minutes. The mixture was then heated to 60° C. and stirred under nitrogen for 30 minutes. After this period, a MCT-NMP mixture, containing 10 g of MCT (63.8 mmol) and 7.3 g of NMP (73.6 mmol), was added, and the mixture was stirred for an additional 15 minutes. Then, the temperature was raised to 70° C., and potassium cyanide (8.5 g, 130 mmol, ground) was added in small portions over a period of 4 hours. Upon the completion of the addition, the resulting mixture was stirred at 70° C. for 24 hours. GC analysis showed that at the end of this period the composition of the mixture was (area % by FID): CT 1.28%, MCT 3.37%, CMT 92.60%, 2,6-dimethoxytoluene (DMT) 2.13%.

EXAMPLE 8

Hydrolysis of 2-Cyano-6-methoxytoluene (CMT) to 3-Methoxy-2-methylbenzoic Acid (MMBA)

To a 3-necked, 25 mL flask, equipped with a temperature controller, a condenser, and a magnetic stirrer, were charged 1.2 g of 2-cyano-6-methoxytoluene (8.2 mmol), 2.0 g of 45% aqueous potassium hydroxide (16.1 mmol), and 15 g of ethylene glycol. The mixture was heated to reflux and stirred for 5 hours. The resulting mixture was cooled to ambient temperatures, diluted with 30 mL of water, and extracted with methylene chloride (2×20 mL). The aqueous layer was acidified with 37% hydrochloric acid until pH was below 2, and then it was extracted with methylene chloride (2×30 mL). The methylene chloride extracts were combined. After methylene chloride was removed, 1.2 g of MMBA was obtained. Yield: 89%.

EXAMPLE 9

Procedure for Converting 3-Methoxy-2-methylbenzoic Acid to 3-Hydroxy-2-methylbenzoic Acid To a 20 mL pressure tube was charged 0.50 g of 3-methoxy-2-methylbenzoic acid (3.0 mmol) and 1.52 g of 48% hydrobromic acid (9.0 mmol, 3.0 eq). The tube was sealed and heated to 170° C. in an oil bath. The mixture was stirred for 4 hours using a magnetic stirrer. It was then cooled to ambient temperature. A portion of the material was stripped to dryness under vacuum to remove volatile components. Analyses of the residue by GC and NMR showed that pure 3-hydroxy-2-methylbenzoic acid was obtained.

EXAMPLE 10

Procedure for Converting 2-Cyano-6-methoxytoluene to 2-Cyano-6-hydroxytoluene

To a 20 mL pressure tube was charged 0.50 g of 2-cyano-6-methoxytoluene (3.4 mmol) and 1.73 g of 48% hydrobromic acid (10.2 mmol, 3.0 eq). The tube was sealed and heated to 170° C. in an oil bath. The mixture was stirred for 4 hours using a magnetic stirrer. It was then cooled to ambient temperature. A portion of the material was stripped to dryness under vacuum to remove volatile components. Analyses of the residue by GC and NMR showed that pure 2-cyano-6-hydroxytoluene was obtained.

EXAMPLE 11

Procedure for Converting 2-Cyano-6-methoxytoluene to 3-Hydroxy-2-methylbenzoic Acid To a 20 mL pressure tube is charged 0.50 g of 2-cyano-6-methoxytoluene and 2.53 g of aqueous 48% hydrobromic acid (17.0 mmol, 5.0 eq). The tube is then sealed and heated to 200° C. The mixture is stirred for 24 hours and then cooled to ambient temperature, extracted with methylene chloride, and the resulting solution washed with water. After the methylene chloride is removed, pure 3-hydroxy-2-methylbenzoic acid is obtained.

EXAMPLE 12

Procedure for Converting 3-Hydroxy-2-methylbenzoic Acid to 3-Acetoxy-2-methylbenzoic Acid To a 50 mL, 3-necked flask, equipped with a reflux condenser, a heating source, a magnetic stirrer, and an addition funnel, were charged 5.00 g of 3-hydroxy-2-methylbenzoic acid (32.9 mmol), and 10 mL of ethyl acetate. The mixture was stirred at 30° C. until HMBA was dissolved. Acetic anhydride (7.50 g, 73.5 mmol) was then added through the addition funnel in 10 minutes. The resulting mixture was stirred at 50° C. for 30 hours. GC analysis showed that at the end of this period the composition of the mixture was (area % by FID): 3-acetoxy-2-methylbenzoic acid 93.32%, 3-hydroxy-2-methylbenzoic acid 0.13%.

EXAMPLE 13

Procedure for Converting 3-Hydroxy-2-methylbenzoic Acid to 3-Acetoxy-2-methylbenzoic Acid To a 100 mL, 3-necked flask, equipped with a reflux condenser, a heating source, a magnetic stirrer, and an addition funnel, were charged 5.72 g of 3-hydroxy-2-methylbenzoic acid (37.6 mmol), 1.0 g of pyridine (12.6 mmol), and 20 mL of ethyl acetate. The mixture was stirred at ambient temperature until the 3-hydroxy-2-methylbenzoic acid was dissolved. Acetic anhydride (4.80 g, 47.0 mmol) was then added through the addition funnel in 10 minutes. The resulting mixture was stirred at 30° C. for 3 hours, and 50° C. for 2 hours. GC analysis showed that at the end of this period the composition of the mixture was (area % by FID): 3-acetoxy-2-methylbenzoic acid 96.52%, 3-hydroxy-2-methylbenzoic acid 0.52%.

It is to be understood that changes and variations in this invention may be made without departing from the spirit and scope of this invention as defined by the appended claims.

We claim:

1. A process for the preparation of a compound of formula (III) comprising the steps of (i) reacting a compound of formula (I) with an alkali or alkaline earth alkoxide, alkali or alkaline earth aroxide, alkali or alkaline earth arylalkoxide, or alkali or alkaline earth heteroarylalkoxide, optionally in the presence of a catalyst comprising copper, to provide a compound of formula (IIa)

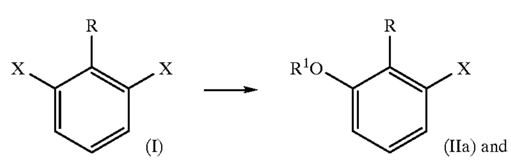

(ii) reacting a compound of formula (IIa) with an alkali or alkaline earth metal cyanide, an aldehyde or ketone cyanohydrin or hydrogen cyanide in the presence of a catalyst comprising nickel, cobalt, palladium or platinum, or reacting a compound of formula (IIa) with copper(I) cyanide in the optional presence of a catalyst comprising nickel, cobalt, palladium or platinum to form an aromatic cyano compound of formula (III)

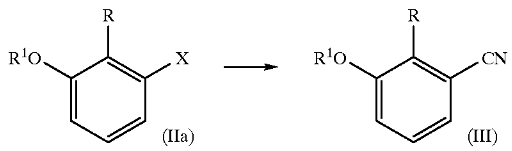

wherein each X is independently triflyl;

R is a hydrogen atom, $(C_1-C_6)$alkyl, aryl, aryl$(C_1-C_2)$alkyl, heteroaryl or heteroaryl$(C_1-C_2)$alkyl; or a $(C_1-C_6)$alkyl, aryl, aryl$(C_1-C_2)$alkyl, heteroaryl or heteroaryl$(C_1-C_2)$alkyl substituted with from one to three substituents independently selected from $(C_1-C_3)$alkyl and $(C_1-C_3)$alkoxy;

$R^1$ is $CHR^2R^3$, aryl, aryl$(C_1-C_2)$alkyl or heteroaryl $(C_1-C_2)$alkyl; or aryl, aryl$(C_1-C_2)$alkyl or heteroaryl $(C_1-C_2)$alkyl substituted with from one to three substituents independently selected from $(C_1-C_3)$alkyl and $(C_1-C_3)$alkoxy; and $R^2$ and $R^3$ are each independently a hydrogen atom, $(C_1-C_5)$alkyl or $(C_1-C_3)$alkyl substituted with $(C_1-C_2)$alkoxy.

2. A process for the preparation of a compound of formula (III) comprising the steps of (i) reacting a compound of formula (I) with an alkali or alkaline earth metal cyanide, an aldehyde or ketone cyanohydrin or hydrogen cyanide in the presence of a catalyst comprising nickel, cobalt, palladium or platinum, or reacting a compound of formula (I) with copper(I) cyanide in the optional presence of a catalyst comprising nickel, cobalt, palladium or platinum to form an aromatic cyano compound of formula (IIb)

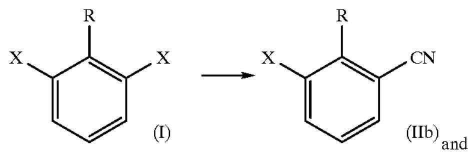

(ii) reacting a compound of formula (IIb) with an alkali or alkaline earth alkoxide, alkali or alkaline earth aroxide, alkali or alkaline earth arylalkoxide, or alkali or alkaline earth heteroarylalkoxide, optionally in the presence of a catalyst comprising copper, to provide a compound of formula (III)

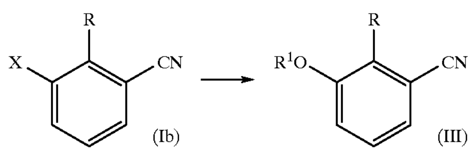

wherein each X is independently triflyl,

R is a hydrogen atom, $(C_1-C_6)$alkyl, aryl, aryl$(C_1-C_2)$alkyl, heteroaryl or heteroaryl$(C_1-C_2)$alkyl; or a $(C_1-C_6)$alkyl, aryl, aryl$(C_1-C_2)$alkyl, heteroaryl or heteroaryl$(C_1-C_2)$alkyl substituted with from one to three substituents independently selected from $(C_1-C_3)$alkyl and $(C_1-C_3)$alkoxy;

$R^1$ is $CHR^2R^3$, aryl, aryl$(C_1-C_2)$alkyl or heteroaryl $(C_1-C_2)$alkyl; or aryl, aryl$(C_1-C_2)$alkyl or heteroaryl $(C_1-C_2)$alkyl substituted with from one to three substituents independently selected from $(C_1-C_3)$alkyl and $(C_1-C_3)$alkoxy; and $R^2$ and $R^3$ are each independently a hydrogen atom, $(C_1-C_5)$alkyl or $(C_1-C_3)$alkyl substituted with $(C_1-C_2)$alkoxy.

3. The process of claims 1 or 2 further comprising a porocess for the preparation of a compound of formula (V) by reacting a compound of formula (III) in a single step with a strong acid which acts both as an ether cleavage reagent and as a nitrile hydrolysis reagent

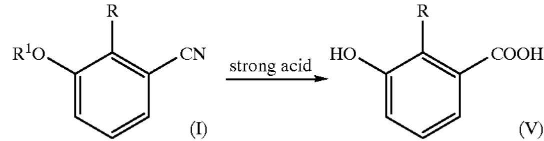

wherein

R is a hydrogen atom, $(C_1-C_6)$alkyl, aryl, aryl$(C_1-C_2)$alkyl, heteroaryl or heteroaryl$(C_1-C_2)$alkyl; or a $(C_1-C_6)$alkyl, aryl, aryl$(C_1-C_2)$alkyl, heteroaryl or heteroaryl$(C_1-C_2)$alkyl substituted with from one to three substituents independently selected from $(C_1-C_3)$alkyl and $(C_1-C_3)$alkoxy;

$R^1$ is $CHR^2R^3$, aryl, aryl$(C_1-C_2)$alkyl or heteroaryl $(C_1-C_2)$alkyl; or aryl, aryl$(C_1-C_2)$alkyl or heteroaryl $(C_1-C_2)$alkyl substituted with from one to three substituents independently selected from $(C_1-C_3)$alkyl and $(C_1-C_3)$alkoxy;

$R^2$ and $R^3$ are each independently a hydrogen atom, $(C_1-C_5)$alkyl or $(C_1-C_3)$alkyl substituted with $(C_1-C_2)$alkoxy, and the strong acid is an aqueous solution of hydrobromic acid or hydroiodic acid.

4. The process of claim 3 wherein

R is a hydrogen atom or $(C_1-C_6)$alkyl;

$R^1$ is $CHR^2R^3$, aryl or aryl$(C_1-C_2)$alkyl; and $R^2$ and $R^3$ are each independently a hydrogen atom or $(C_1-C_2)$alkyl, or $(C_1-C_2)$alkyl substituted with methoxy.

5. The process of claim 4 wherein R is a hydrogen atom or $(C_1-C_3)$alkyl, $R^1$ is $CHR^2R^3$, and $R^2$ and $R^3$ are each independently a hydrogen atom or $(C_1-C_2)$alkyl.

6. The process of claim 5 wherein R is methyl or ethyl, $R^2$ is a hydrogen atom, and $R^3$ is a hydrogen atom or methyl.

7. The process of claims 1 or 2 further comprising the preparation of a compound of formula (VI) by hydrolyzing a compound of formula (III) to form a compound of formula (IVa) by reacting with a strong acid or base

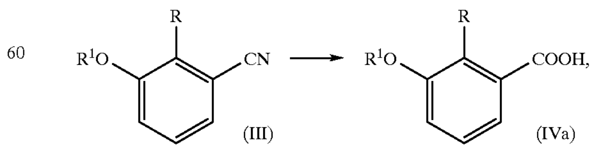

converting a compound of formula (IVa) to a compound of formula (V) by reacting with an ether cleavage reagent

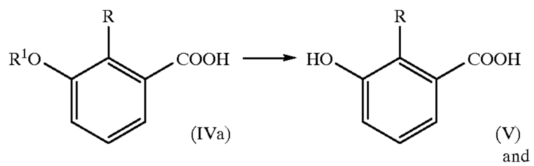

and reacting a compound of formula (V) with an organic acid anhydride

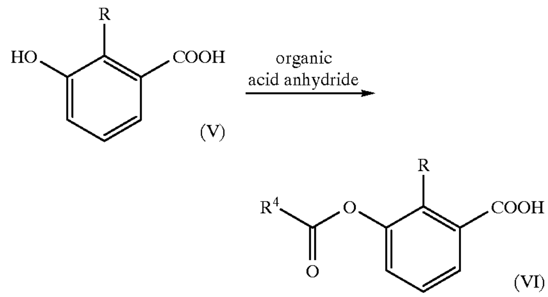

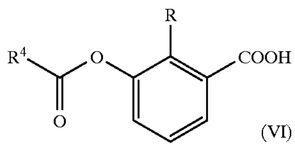

wherein

R is a hydrogen atom, $(C_1-C_6)$alkyl, aryl, aryl$(C_1-C_2)$alkyl, heteroaryl or heteroaryl$(C_1-C_2)$alkyl; or a $(C_1-C_6)$alkyl, aryl, aryl$(C_1-C_2)$alkyl, heteroaryl or heteroaryl$(C_1-C_2)$alkyl substituted with from one to three substituents independently selected from $(C_1-C_3)$alkyl and $(C_1-C_3)$alkoxy;

$R^1$ is $CHR^2R^3$ aryl, aryl$(C_1-C_2)$alkyl or heteroaryl$(C_1-C_2)$alkyl; or aryl, aryl$(C_1-C_2)$alkyl or heteroaryl$(C_1-C_2)$alkyl substituted with from one to three substituents independently selected from $(C_1-C_3)$alkyl and $(C_1-C_3)$alkoxy;

$R^2$ and $R^3$ are each independently a hydrogen atom, $(C_1-C_5)$alkyl or $(C_1-C_3)$alkyl substituted with $(C_1-C_2)$alkoxy;

$R^4$ is a hydrogen atom or $(C_1-C_3)$alkyl; and the organic acid anhydride is formic anhydride, acetic anhydride, a propionic anhydride or a butyric anhydride.

8. The process of claim 7 wherein R is a hydrogen atom or $(C_1-C_6)$alkyl; and $R^4$ is $(C_1-C_3)$alkyl.

9. The process of claim 8 wherein R is a hydrogen atom or $(C_1-C_3)$alkyl and $R^4$ is $(C_1-C_2)$alkyl.

10. The process of claim 9 wherein R is methyl or ethyl and $R^4$ is methyl.

11. The process of claims 1 or 2 further comprising the preparation of a compound of formula (VI) by reacting a compound of formula (III) with an ether cleavage reagent in a first step

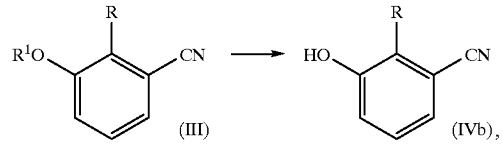

hydrolyzing a compound of formula (IVb) using a strong acid or base to a compound of formula (V) in a second step

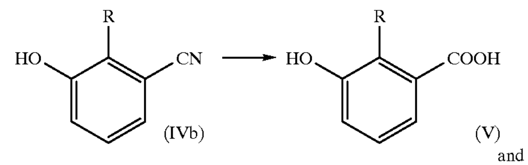

and reacting a compound of formula (V) with an organic acid anhydride to form a compound of formula (VI)

wherein

R is a hydrogen atom, $(C_1-C_6)$alkyl, aryl, aryl$(C_1-C_2)$alkyl, heteroaryl or heteroaryl$(C_1-C_2)$alkyl; or a $(C_1-C_6)$alkyl, aryl, aryl$(C_1-C_2)$alkyl, heteroaryl or heteroaryl$(C_1-C_2)$alkyl substituted with from one to three substituents independently selected from $(C_1-C_3)$alkyl and $(C_1-C_3)$alkoxy;

$R^1$ is $CHR^2R^3$, aryl, aryl$(C_1-C_2)$alkyl or heteroaryl$(C_1-C_2)$alkyl; or aryl, aryl$(C_1-C_2)$alkyl or heteroaryl$(C_1-C_2)$alkyl substituted with from one to three substituents independently selected from $(C_1-C_3)$alkyl and $(C_1-C_3)$alkoxy;

$R^2$ and $R^3$ are each independently a hydrogen atom, $(C_1-C_5)$alkyl or $(C_1-C_3)$alkyl substituted with $(C_1-C_2)$alkoxy;

$R^4$ is a hydrogen atom or $(C_1-C_3)$alkyl; and the organic acid anhydride is formic anhydride, acetic anhydride, a propionic anhydride or a butyric anhydride.

12. The process of claim 11 wherein R is a hydrogen atom or $(C_1-C_6)$alkyl; and $R^4$ is $(C_1-C_3)$alkyl.

13. The process of claim 12 wherein R is a hydrogen atom or $(C_1-C_3)$alkyl and $R^4$ is $(C_1-C_2)$alkyl.

14. The process of claim 13 wherein R is methyl or ethyl and $R^4$ is methyl.

15. The process of claim 3 further comprising the preparation of a compound of formula (VI) by reacting a compound of formula (V) with an organic acid anhydride

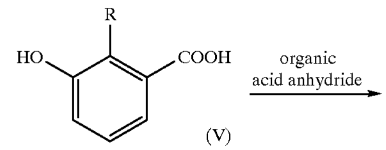

-continued

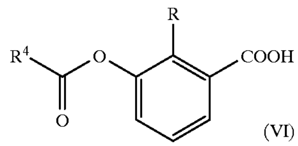

wherein

R is a hydrogen atom, $(C_1-C_6)$alkyl, aryl, aryl$(C_1-C_2)$ alkyl, heteroaryl or heteroaryl$(C_1-C_2)$alkyl; or a $(C_1-C_6)$alkyl, aryl, aryl$(C_1-C_2)$alkyl, heteroaryl or heteroaryl$(C_1-C_2)$alkyl substituted with from one to three substituents independently selected from $(C_1-C_3)$ alkyl and $(C_1-C_3)$alkoxy;

$R^4$ is a hydrogen atom or $(C_1-C_3)$alkyl; and the organic acid anhydride is formic anhydride, acetic anhydride, a propionic anhydride or a butyric anhydride.

16. The process of claim 15 wherein R is a hydrogen atom or $(C_1-C_6)$alkyl; and $R^4$ is $(C_1-C_3)$alkyl.

17. The process of claim 16 wherein R is a hydrogen atom or $(C_1-C_3)$alkyl and $R^4$ is $(C_1-C_2)$alkyl.

18. The process of claim 17 wherein R is methyl or ethyl and $R^4$ is methyl.

19. A process for the preparation of a compound of formula (III) comprising reacting a compound of formula (IIa) with an alkali or alkaline earth metal cyanide, an aldehyde or ketone cyanohydrin or hydrogen cyanide in the presence of a catalyst comprising nickel, cobalt, palladium or platinum, or reacting a compound of formula (IIa) with copper(I) cyanide in the optional presence of a catalyst comprising nickel, cobalt, palladium or platinum to form an aromatic cyano compound of formula (III)

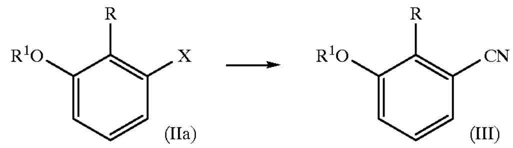

wherein

X is triflyl;

R is a hydrogen atom, $(C_1-C_6)$alkyl, aryl, aryl$(C_1-C_2)$ alkyl, heteroaryl or heteroaryl$(C_1-C_2)$alkyl; or a $(C_1-C_6)$alkyl, aryl, aryl$(C_1-C_2)$alkyl, heteroaryl or heteroaryl$(C_1-C_2)$alkyl substituted with from one to three substittuents independently selected from $(C_1-C_3)$alkyl and $(C_1-C_3)$alkoxy;

$R^1$ is $CHR^2R^3$, aryl, aryl$(C_1-C_2)$alkyl or heteroaryl $(C_1-C_2)$alkyl; or aryl, aryl$(C_1-C_2)$alkyl or heteroaryl $(C_1-C_2)$alkyl substituted with from one to three substituents independently selected from $(C_1-C_3)$alkyl and $(C_1-C_3)$alkoxy; and $R^2$ and $R^3$ are each independently a hydrogen atom, $(C_1-C_5)$alkyl or $(C_1-C_3)$alkyl substituted with $(C_1-C_2)$ alkoxy.

20. A process for the preparation of a compound of formula (III) comprising reacting a compound of formula (IIb) with an alkali or alkaline earth alkoxide, alkali or alkaline earth aroxide, alkali or alkaline earth arylalkoxide, or alkali or alkaline earth heteroarylalkoxide, optionally in the presence of a catalyst comprising copper, to provide a compound of formula (III)

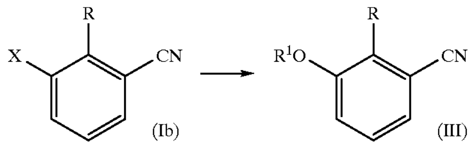

wherein

X is triflyl;

R is a hydrogen atom, $(C_1-C_6)$alkyl, aryl, aryl$(C_1-C_2)$ alkyl, heteroaryl or heteroaryl$(C_1-C_2)$alkyl; or a $(C_1-C_6)$alkyl, aryl, aryl$(C_1-C_2)$alkyl, heteroaryl or heteroaryl$(C_1-C_2)$alkyl substituted with from one to three substituents independently selected from $(C_1-C_3)$ alkyl and $(C_1-C_3)$alkoxy;

$R^1$ is $CHR^2R^3$, aryl, aryl$(C_1-C_2)$alkyl or heteroaryl $(C_1-C_2)$alkyl; or aryl, aryl$(C_1-C_2)$alkyl or heteroaryl $(C_1-C_2)$alkyl substituted with from one to three substituents independently selected from $(C_1-C_3)$alkyl and $(C_1-C_3)$alkoxy; and $R^2$ and $R^3$ are each independently a hydrogen atom, $(C_1-C_5)$alkyl or $(C_1-C_3)$alkyl substituted with $(C_1-C_2)$ alkoxy.

21. The process of claims 19 or 20 further comprising the preparation of a compound of formula (IVa) by hydrolyzing a compound of formula (III) using a strong acid or base

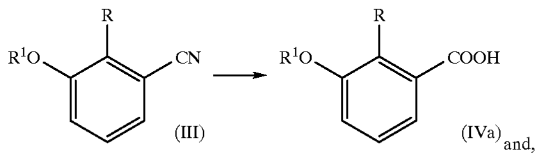

if desired, further converting a compound of formula (IVa) to a compound of formula (V) using an ether cleavage reagent

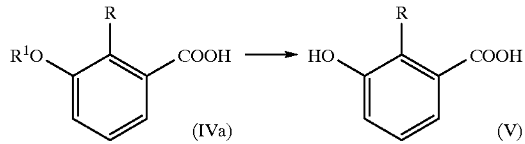

wherein

R is a hydrogen atom, $(C_1-C_6)$alkyl, aryl, aryl$(C_1-C_2)$ alkyl, heteroaryl or heteroaryl$(C_1-C_2)$alkyl; or a $(C_1-C_6)$alkyl, aryl, aryl$(C_1-C_2)$alkyl, heteroaryl or heteroaryl$(C_1-C_2)$alkyl substituted with from one to three substituents independently selected from $(C_1-C_3)$ alkyl and $(C_1-C_3)$alkoxy;

$R^1$is $CHR^2R^3$, aryl, aryl$(C_1-C_2)$alkyl or heteroaryl $(C_1-C_2)$alkyl; or aryl, aryl$(C_1-C_2)$alkyl or heteroaryl $(C_1-C_2)$alkyl substituted with from one to three substituents independently selected from $(C_1-C_3)$alkyl and $(C_1-C_3)$alkoxy; and $R^2$ and $R^3$ are each independently a hydrogen atom, $(C_1-C_5)$alkyl or $(C_1-C_3)$alkyl substituted with $(C_1-C_2)$ alkoxy.

22. The process of claims 19 or 20 further comprising the preparation of a compound of formula (IVb) by reacting a compound of formula (III) with an ether cleavage reagent in a first step

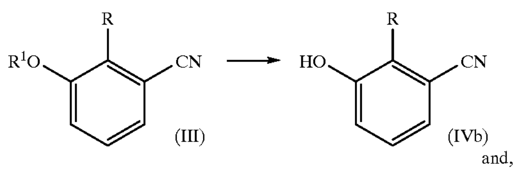

if desired, hydrolyzing a compound of formula (IVb) using a strong acid or base to a compound of formula (V) in a second step

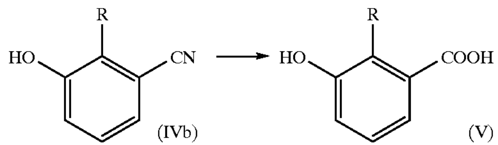

wherein

R is a hydrogen atom, $(C_1–C_6)$alkyl, aryl, aryl$(C_1–C_2)$alkyl, heteroaryl or heteroaryl$(C_1–C_2)$alkyl; or a $(C_1–C_6)$alkyl, aryl, aryl$(C_1–C_2)$alkyl, heteroaryl or heteroaryl$(C_1–C_2)$alkyl substituted with from one to three substituents independently selected from $(C_1–C_3)$alkyl and $(C_1–C_3)$alkoxy;

$R^1$ is $CHR^2R^3$, aryl, aryl$(C_1–C_2)$alkyl or heteroaryl$(C_1–C_2)$alkyl; or aryl, aryl$(C_1–C_2)$alkyl or heteroaryl$(C_1–C_2)$alkyl substituted with from one to three substituents independently selected from $(C_1–C_3)$alkyl and $(C_1–C_3)$alkoxy; and $R^2$ and $R^3$ are each independently a hydrogen atom, $(C_1–C_5)$alkyl or $(C_1–C_3)$alkyl substituted with $(C_1–C_2)$alkoxy.

23. The process of claims 19 or 20 wherein

X is chloro or bromo;

R is a hydrogen atom or $(C_1–C_6)$alkyl;

$R^1$ is $CHR^2R^3$, aryl or aryl$(C_1–C_2)$alkyl; and $R^2$ and $R^3$ are each independently a hydrogen atom or $(C_1–C_2)$alkyl, or $(C_1–C_2)$alkyl substituted with methoxy.

24. The process of claim 23 wherein R is a hydrogen atom or $(C_1–C_3)$alkyl, $R^1$ is $CHR^2R^3$, and $R^2$ and $R^3$ are each independently a hydrogen atom or $(C_1–C_2)$alkyl.

25. The process of claim 24 wherein R is methyl or ethyl, $R^2$ is a hydrogen atom, and $R^3$ is a hydrogen atom or methyl.

26. The process of claims 19 or 20 further comprising a process for the preparation of a compound of formula (V) by reacting a compound of formula (III) in a single step with a strong acid which acts both as an ether cleavage reagent and as a nitrile hydrolysis reagent

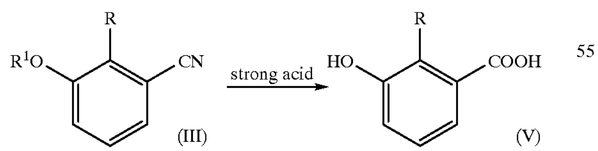

wherein

R is a hydrogen atom, $(C_1–C_6)$alkyl, aryl, aryl$(C_1–C_2)$alkyl, heteroaryl or heteroaryl$(C_1–C_2)$alkyl; or a $(C_1–C_6)$alkyl, aryl, aryl$(C_1–C_2)$alkyl, heteroaryl or heteroaryl$(C_1–C_2)$alkyl substituted with from one to three substituents independently selected from $(C_1–C_3)$alkyl and $(C_1–C_3)$alkoxy;

$R^1$ is $CHR^2R^3$, aryl, aryl$(C_1–C_2)$alkyl or heteroaryl$(C_1–C_2)$alkyl; or aryl, aryl$(C_1–C_2)$alkyl or heteroaryl$(C_1–C_2)$alkyl substituted with from one to three substituents independently selected from $(C_1–C_3)$alkyl and $(C_1–C_3)$alkoxy;

$R^2$ and $R^3$ are each independently a hydrogen atom, $(C_1–C_5)$alkyl or $(C_1–C_3)$alkyl substituted with $(C_1–C_2)$alkoxy, and the strong acid is an aqueous solution of hydrobromic acid or hydroiodic acid.

27. The process of claim 26 wherein

R is a hydrogen atom or $(C_1–C_6)$alkyl;

$R^1$ is $CHR^2R^3$, aryl or aryl$(C_1–C_2)$alkyl; and $R^2$ and $R^3$ are each independently a hydrogen atom or $(C_1–C_2)$alkyl, or $(C_1–C_2)$alkyl substituted with methoxy.

28. The process of claim 27 wherein R is a hydrogen atom or $(C_1–C_3)$alkyl, $R^1$ is $CHR^2R^3$, and $R^2$ and $R^3$ are each independently a hydrogen atom or $(C_1–C_2)$alkyl.

29. The process of claim 28 wherein R is methyl or ethyl, $R^2$ is a hydrogen atom, and $R^3$ is a hydrogen atom or methyl.

30. The process of claims 19 or 20 further comprising the preparation of a compound of formula (VI) by hydrolyzing a compound of formula (III) to a compound of formula (IVa) using a strong acid or base

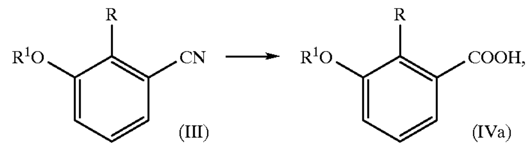

converting a compound of formula (IVa) to a compound of formula (V) using an ether cleavage reagent

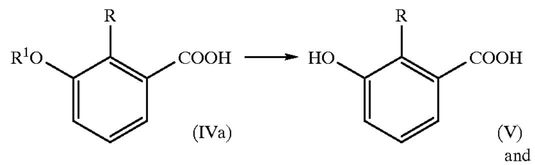

and reacting a compound of formula (V) with an organic acid anhydride

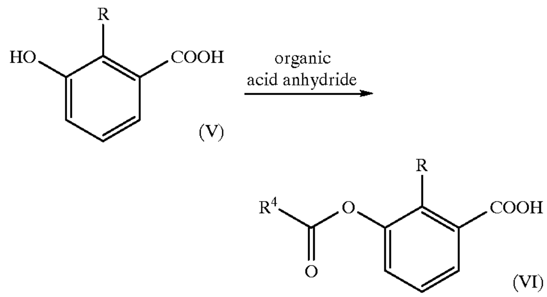

wherein

R is a hydrogen atom, $(C_1–C_6)$alkyl, aryl, aryl$(C_1–C_2)$alkyl, heteroaryl or heteroaryl$(C_1–C_2)$alkyl; or a $(C_1–C_6)$alkyl, aryl, aryl$(C_1–C_2)$alkyl, heteroaryl or heteroaryl$(C_1–C_2)$alkyl substituted with from one to three substituents independently selected from $(C_1–C_3)$alkyl and $(C_1–C_3)$alkoxy;

$R^1$ is $CHR^2R^3$, aryl, aryl($C_1$–$C_2$)alkyl or heteroaryl ($C_1$–$C_2$)alkyl; or aryl, aryl($C_1$–$C_2$)alkyl or heteroaryl ($C_1$–$C_2$)alkyl substituted with from one to three substituents independently selected from ($C_1$–$C_3$)alkyl and ($C_1$–$C_3$)alkoxy;

$R^2$ and $R^3$ are each independently a hydroaen atom, ($C_1$–$C_5$)alkyl or ($C_1$–$C_3$)alkyl substituted with ($C_1$–$C_2$) alkoxy;

$R^4$ is a hydrogen atom or ($C_1$–$C_3$)alkyl; and the organic acid anhydride is formic anhydride, acetic anhydride, a propionic anhydride or a butyric anhydride.

31. The process of claim 29 wherein R is a hydrogen atom or ($C_1$–$C_6$)alkyl; and $R^4$ is ($C_1$–$C_3$)alkyl.

32. The process of claim 31 wherein R is a hydrogen atom or ($C_1$–$C_3$)alkyl and $R^4$ is ($C_1$–$C_2$)alkyl.

33. The process of claim 32 wherein R is methyl or ethyl and $R^4$ is methyl.

34. The process of claims 19 or 20 further comprising the preparation of a compound of formula (VI) by reacting a compound of formula (III) with an ether cleavage reagent to form a compound of formula (IVb),

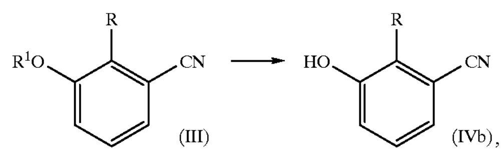

hydrolyzing a compound of formula (IVb) using a strong acid or base to a compound of formula (V)

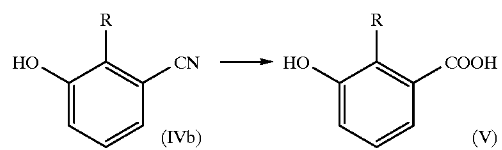

reacting a compound of formula (V) with an organic acid anhydride

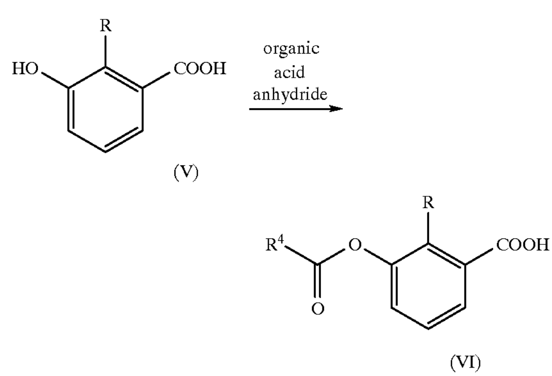

wherein

R is a hydrogen atom, ($C_1$–$C_6$)alkyl, aryl, aryl($C_1$–$C_2$) alkyl, heteroaryl or heteroaryl($C_1$–$C_2$)alkyl; or a ($C_1$–$C_6$)alkyl, aryl, aryl($C_1$–$C_2$)alkyl, heteroaryl or heteroaryl($C_1$–$C_2$)alkyl substituted with from one to three substituents independently selected from ($C_1$–$C_3$) alkyl and ($C_1$–$C_3$)alkoxy;

$R^1$ is $CHR^2R^3$, aryl, aryl($C_1$–$C_2$)alkyl or heteroaryl ($C_1$–$C_2$)alkyl; or aryl, aryl($C_1$–$C_2$)alkyl or heteroaryl ($C_1$–$C_2$)alkyl substituted with from one to three substituents independently selected from ($C_1$–$C_3$)alkyl and ($C_1$–$C_3$)alkoxy;

$R^2$ and $R^3$ are each independently a hydroaen atom, ($C_1$–$C_5$)alkyl or ($C_1$–$C_3$)alkyl substituted with ($C_1$–$C_2$) alkoxy;

$R^4$ is a hydrogen atom or ($C_1$–$C_3$)alkyl; and the organic acid anhydride is formic anhydride, acetic anhydride, a propionic anhydride or a butyric anhydride.

35. The process of claim 34 wherein R is a hydrogen atom or ($C_1$–$C_6$)alkyl; and $R^4$ is ($C_1$–$C_3$)alkyl.

36. The process of claim 35 wherein R is a hydrogen atom or ($C_1$–$C_3$)alkyl and $R^4$ is ($C_1$–$C_2$)alkyl.

37. The process of claim 36 wherein R is methyl or ethyl and $R^4$ is methyl.

38. The process of claims 19 or 20 further comprising the preparation of a compound of formula (VI) by reacting a compound of formula (III) in a single step with a strong acid which acts both as an ether cleavage reagent and as a nitrile hydrolysis reagent to form a compound of formula (V)

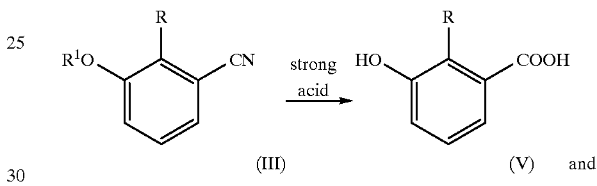

racting a compound of formula (V) with an organic acid anhydride

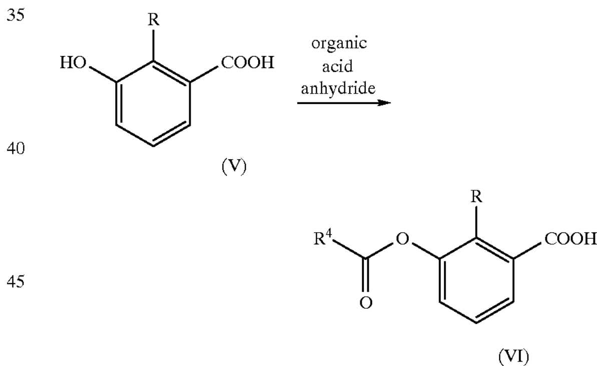

R is a hydrogen atom, ($C_1$–$C_6$)alkyl, aryl, aryl($C_1$–$C_2$) alkyl, heteroaryl or heteroaryl($C_1$–$C_2$)alkyl; or a ($C_1$–$C_6$)alkyl, aryl, aryl($C_1$–$C_2$)alkyl, heteroaryl or heteroaryl($C_1$–$C_2$)alkyl substituted with from one to three substituents independently selected from ($C_1$–$C_3$) alkyl and ($C_1$–$C_3$)alkoxy;

$R^1$ is $CHR^2R^3$, aryl, aryl($C_1$–$C_2$)alkyl or heteroaryl ($C_1$–$C_2$)alkyl; or aryl, aryl($C_1$–$C_2$ alkyl or heteroaryl ($C_1$–$C_2$)alkyl substituted with from one to three substituents independently selected from ($C_1$–$C_3$)alkyl and ($C_1$–$C_3$)alkoxy;

$R^2$ and $R^3$ are each independently a hydrogen atom, ($C_1$–$C_5$)alkyl or ($C_1$–$C_3$)alkyl substituted with ($C_1$–$C_2$) alkoxy;

$R^4$ is a hydrogen atom or ($C_1$–$C_3$)alkyl; and the organic acid anhydride is formic anhydride, acetic anhydride, a propionic anhydride or a butyric anhydride.

39. The process of claim 33 wherein R is a hydrogen atom or $(C_1-C_6)$alkyl; and $R^4$ is $(C_1-C_3)$alkyl.

40. The process of claim 39 wherein R is a hydrogen atom or $(C_1-C_3)$alkyl and $R^4$ is $(C_1-C_2)$alkyl.

41. The process of claim 40 wherein R is methyl or ethyl and $R^4$ is methyl.

42. The process of claim 7 further comprising the use of a tertiary amine catalyst.

43. The process of claim 42 wherein the catalyst is pyridine, quinoline, a picoline, N-methylpyrrole, N-methylpyrrolidine or a trialkylamine.

44. The process of claim 43 wherein the catalyst is pyridine or triethylamine.

45. The process of claim 11 further comprising the use of a tertiary amine catalyst in the step to form a compound of formula (VI).

46. The process of claim 45 wherein the catalyst is pyridine, quinoline, a picoline, N-methylpyrrole, N-methylpyrrolidine or a trialkylamine.

47. The process of claim 46 wherein the catalyst is pyridine or triethylamine.

48. The process of claim 15 further comprising the use of a tertiary amine catalyst.

49. The process of claim 48 wherein the catalyst is pyridine, quinoline, a picoline, N-methylpyrrole, N-methylpyrrolidine or a trialkylamine.

50. The process of claim 49 wherein the catalyst is pyridine or triethylamine.

51. The process of claim 30 further comprising the use of a tertiary amine catalyst in the step to form a compound of formula (VI).

52. The process of claim 51 wherein the catalyst is pyridine, quinoline, a picoline, N-methylpyrrole, N-methylpyrrolidine or a trialkylamine.

53. The process of claim 52 wherein the catalyst is pyridine or triethylamine.

54. The process of claim 34 further comprising the use of a tertiary amine catalyst in the step to form a compound of formula (VI).

55. The process of claim 54 wherein the catalyst is pyridine, quinoline, a picoline, N-methylpyrrole, N-methylpyrrolidine or a trialkylamine.

56. The process of claim 55 wherein the catalyst is pyridine or triethylamine.

57. The process of claim 38 further comprising the use of a tertiary amine catalyst in the step to form a compound of formula (VI).

58. The process of claim 57 wherein the catalyst is pyridine, quinoline, a picoline, N-methylpyrrole, N-methylpyrrolidine or a trialkylamine.

59. The process of claim 58 wherein the catalyst is pyridine or triethylamine.

* * * * *